United States Patent [19]

Gromes

[11] Patent Number: 5,686,260
[45] Date of Patent: Nov. 11, 1997

[54] METHOD AND COMPOSITION FOR THE ENZYMIC DETERMINATION OF ASPARTAME

[75] Inventor: Reiner Gromes, Gross-Umstadt, Germany

[73] Assignee: Merck Patent Gesellschaft Mit Beschrankter Haftung, Darmstadt, Germany

[21] Appl. No.: 554,462

[22] Filed: Nov. 7, 1995

Related U.S. Application Data

[63] Continuation of Ser. No. 286,182, Aug. 5, 1994, abandoned.

[30] Foreign Application Priority Data

Aug. 6, 1993 [DE] Germany ............ 43 26 419.0

[51] Int. Cl.[6] .................. C12Q 1/37; C12Q 1/00
[52] U.S. Cl. .................. 435/23; 435/4; 435/16; 435/24; 435/25; 435/26; 435/288; 435/808; 435/810
[58] Field of Search .................. 435/23, 4, 16, 435/24, 25, 26, 288, 808, 810

[56] References Cited

U.S. PATENT DOCUMENTS

| | | | |
|---|---|---|---|
| 5,279,945 | 1/1994 | Hummel | 435/24 |
| 5,429,726 | 7/1995 | Johnson et al. | 204/153.12 |

OTHER PUBLICATIONS

Boki et al, *Jpn. J. Toxicol. Environm. Health*, vol. 39, No. 1, pp. 72–75, 1993.

Mulchandani et al, *Analytica Chimica Acta*, vol. 234, pp. 465–469, 1990.

Boki et al, *Chemical Abstracts*, vol. 118, p. 755, Ref. #167757u, 1993 (Jpn. J. Toxicol. Environ. Health 1993 39(1) 72–75).

*Primary Examiner*—Robert J. Hill, Jr.
*Assistant Examiner*—Abdel A. Mohamed
*Attorney, Agent, or Firm*—Millen, White, Zelano, & Branigan, P.C.

[57] ABSTRACT

The invention relates to a method and a composition for the enzymic determination of aspartame in aqueous solutions. The method is carried out such that the sample solution is incubated essentially in the presence of oxo-glutarate, glutamate-oxaloacetate transaminase (GOT), malate dehydrogenase (MDH), NADH and a protease, and the decrease in the NADH extinction is measured photometrically.

9 Claims, 1 Drawing Sheet

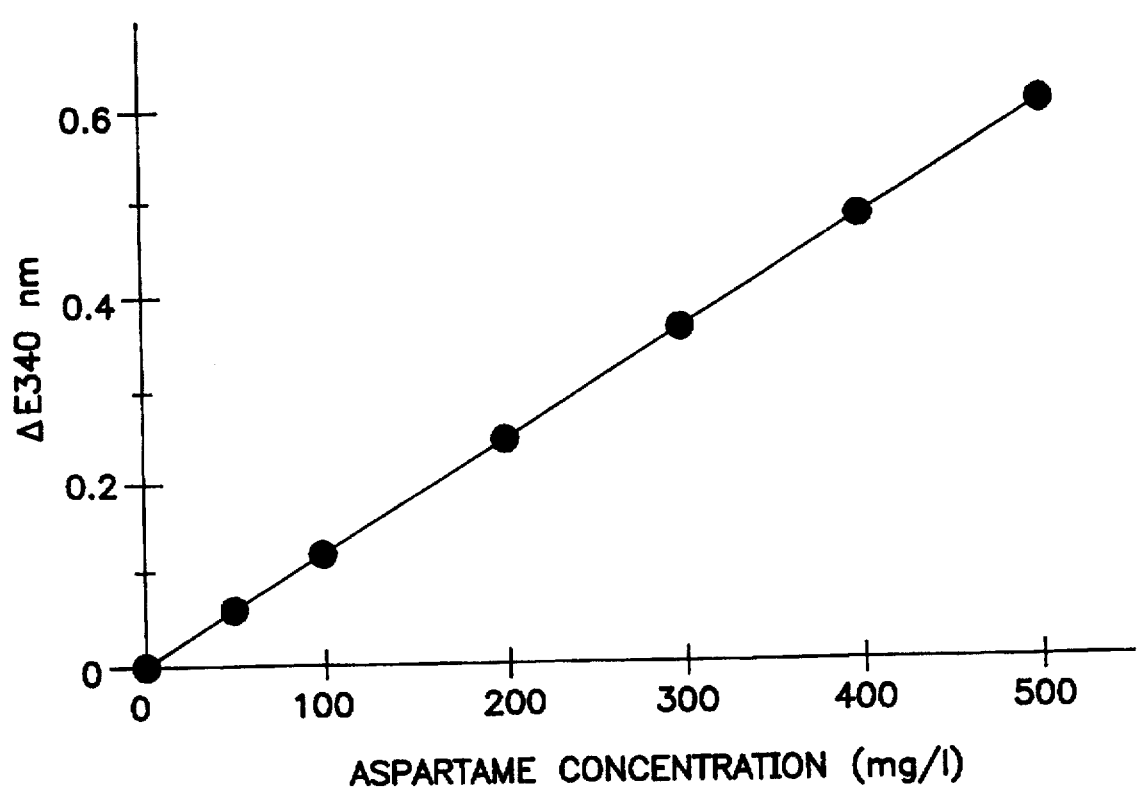

METHOD AND COMPOSITION FOR THE ENZYMIC DETERMINATION OF ASPARTAME

This application is a continuation of application Ser. No. 08/286,182, filed Aug. 5, 1994 now abandoned.

BACKGROUND OF THE INVENTION

The invention relates to a method and a composition for the enzymic determination of aspartame in aqueous solutions.

Aspartame is a dipeptide ester composed of L-aspartic acid and L-phenylalanine methyl ester. Aspartame is about 200 times as sweet as sugar and is employed in many foodstuffs on account of its high sweetening power.

However, owing to the fact that it is not very stable, the options for using the sweetener are limited. Aspartame is only stable in solid form, while in aqueous solutions its stability is greatest at pH values of from 4 to 5. In addition, its stability depends on the temperature and duration of storage. If processed or stored improperly, aspartame can give rise to a variety of degradation products, e.g., aspartic acid, phenylalanine, phenylalanine methyl ester or aspartylphenylalanine.

For this reason, determination of aspartame is of great interest, especially in the quality control of foodstuffs, but also as a process control in the preparation and processing of foodstuffs.

Aspartame can be determined by a variety of chromatographic methods (HPLC, TLC and GC). These determination methods as a rule require special sample-preparation steps and are therefore very time-consuming. In addition, a quite considerable amount of apparatus is needed for the determination.

An alternative is provided by enzymic determination methods. They are simple and rapid and can be carried out with adequate sensitivity and without the need for any large amount of apparatus. If specific enzymes are used, the sample can be added directly to the test system without any special processing steps. Enzymic methods are known, e.g., from Anal. Chim. Acta, 234:465 (1990), for determining aspartame in conjunction with electrodes or sensors. However, these methods suffer from the disadvantage that electrodes or sensors, which have only a limited stability and which are in some cases difficult to obtain, are required for detecting the measurement signal.

Analyst, 115:435 (1990), discloses an enzymic method for determining aspartame in which aspartame, having been enzymically hydrolyzed with a peptidase, is reacted with alcohol oxidase resulting in the formation of formaldehyde. The formaldehyde is reacted with amino-pent-3-en-2-one and the product is purified through a column, with the eluate being measured photometrically. The disadvantages of this method are the relatively large, amount of time required for an analysis due to the purification step for the reaction product and the column material which is required in addition.

DE 40 29 296 describes a method for determining aspartame in which the three enzymes participating in the reaction are spatially separated from each other by immobilization. The enzymic reactions are carried out in successive enzyme columns as a flow-injection analysis with a reaction product being determined fluorimetrically. The evident disadvantages of this method are the requisite immobilization of the three enzymes participating in the determination and the limited stability and availability of the immobilized enzymes. Two special proteases (pronase E and chymotrypsin) are employed for hydrolyzing aspartame in order to liberate the desired reaction product, phenylalanine. According to the present state of the art, it is considered impossible to develop photometric cuvette tests based on these enzymes since two of the enzymes employed are proteases which would mutually inactivate themselves as well as inactivating the phenylalanine dehydrogenase. This method is also not capable of dealing with samples which contain fluorescent compounds since it is only possible to evaluate such samples by fluorescence photometry once they have been subjected to additional sample preparation steps (GIT Fachz. Lab., 3/93, 199 (1992)).

SUMMARY OF THE INVENTION

The present invention is based on the object of making available a method and a composition for the specific determination of aspartame in foodstuffs and biological samples, which method can be carried out using a simple photometric test.

The invention relates to a method for the enzymic determination of aspartame in aqueous solutions, which method is characterized in that the sample solution is incubated essentially in the presence of oxoglutarate, glutamate-oxaloacetate transaminase (GOT), malate dehydrogenase (MDH), nicotinamide adenine dinucleotide (reduced) (NADH) and a protease, and the decrease in the NADH extinction is measured photometrically.

The invention further relates to a composition for the enzymic determination of aspartame in aqueous solutions, which composition essentially contains oxoglutarate, GOT, MDH, NADH and a protease.

BRIEF DESCRIPTION OF THE DRAWINGS

Various other objects, features and attendant advantages of the present invention will be more fully appreciated as the same becomes better understood when considered in conjunction with the accompanying drawing, in which like reference characters designate the same or similar parts throughout the several views, and wherein:

FIG. 1 shows a calibration curve for 0–500 mg/l of aspartame as measured by the difference in extinction at 340 nm, according to the present invention.

DETAILED DESCRIPTION

The literature provides a series of examples of the enzymic determination of the amino acid L-aspartic acid. A method based on a coupled UV test is described in Bergmeyer, "Methods of Enzymatic Analysis," Vol. VIII, pp. 350–357 (1985):

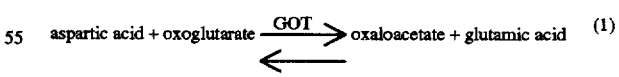

Aspartic acid can be released from aspartame by various proteases:

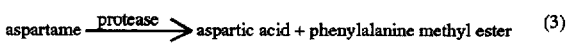

Surprisingly, it has been found that, when suitable reaction conditions are chosen, it is possible to determine aspartame in a single reaction mixture by means of hydrolyzing with a protease and detecting the resulting aspartic acid in accordance with equations (1) and (2). In this case, the samples and aspartame standards are incubated alongside each other under identical reaction conditions (reagents, volumes, time and temperature) and the extinctions are measured at 340 or 365 nm before adding the protease ($E_1$) and at a predetermined time, e.g., 20 minutes, after adding the protease ($E_2$). The difference in extinction ($E_1$-$E_2$) is directly proportional to the aspartame concentration in the range of 0–500 mg/l aspartame. Determination of the aspartame content of unknown samples is thus effected by comparing the extinction differences of the samples and a standard solution of known aspartame concentration, or of aspartame standards of varying concentration using a calibration curve.

The specificity for aspartame is ensured by the sequence of the reactions (1, 2, 3). Large numbers of samples can be determined in parallel alongside each other (approximately 50 samples). The sensitivity is comparable with the methods which have already been described. The advantages of the method according to the invention are that it is simple to carry out without making any great use of complex apparatus and that the reagents used are stable. The method is additionally facilitated by the ready-to-use reagents being made available in solid form (e.g., tablets) as a test kit. In principle, the method according to the invention can also be carried out as a microtiter plate test or on an autoanalyzer. A fluorescence detector can also be employed for the purpose of increasing sensitivity.

In addition to oxoglutarate, NADH and the enzymes, the composition according to the invention preferably also contains pyridoxal 5-phosphate, which, as a coenzyme, optimizes the activity of the transaminase (GOT).

The method according to the invention is preferably carried out in the presence of a buffer which allows the reactions to proceed in an optimal pH range of about 6.5–8.5, preferably at a pH of 7.5. Suitable buffers are those, such as, for example, Tris/HCl buffer, HEPES buffer, imidazole buffer, triethanolamine buffer or PIPES buffer, preferably Tris/HCl buffer, which do not interfere with the course of the reaction. The concentration of the buffer should be in the range from about 50 to 500 mM.

The concentrations of the remaining constituents should be in the following ranges: oxoglutarate, from about 5 to 20 mM, pyridoxal.5-phosphate, from about 0 to 1 mM, NADH, from about 150 to 240 µM, GOT, from about 1 to 10. $^KU/l$ and MDH, from about 10 to 100 $^KU/l$.

The commercially available proteases, such as pronase E, aminopeptidase M, aminopeptidase K, leucine-aminopeptidase or alkalase, preferably pronase E, are suitable for hydrolyzing aspartame. If pronase E is used, its concentration in the test mixture should be from about 0.2 to 2 mg, preferably 1 mg, per mixture (2.4 ml). If less active proteases are used, analogous results are achieved by raising the concentration and/or extending the incubation time.

In accordance with the invention, aspartame is determined in the presence of all the reagents in a single reaction vessel. The incubation is preferably carried out in two steps, incubation with the protease being carried out in the second step. To do this, the sample solution is treated with a reaction solution which contains all the necessary reagents apart from the protease. There is then a waiting period of a few minutes, after which extinction $E_1$ is measured. The protease solution is then added and extinction $E_2$ is measured after an incubation period of from 2 to 60 minutes, preferably of about 20 minutes, at from 15 to 40° C. The parameter measured is the decrease in NADH concentration which is measured at either 340 or 365 nm. The results are evaluated using a calibration curve.

The composition according to the invention is preferably used in the form of a test kit which contains the ready-to-use reagents, e.g., in the form of tablets or lyophilizates. Oxoglutarate, pyridoxal 5-phosphate, NADH and the protease are present, for example, as tablets, aspartame as a lyophilizate and the enzymes GOT and MDH in the form of a suspension. If the sample being investigated contains proteins, it is then advantageous to precipitate these out using the conventional protein-precipitation reagents (e.g., Carrez reagent: potassium hexacyanoferrate and zinc sulfate) and to remove them from the sample solution by centrifugation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 26 419.0, filed Aug. 6, 1993, are hereby incorporated by reference.

EXAMPLES

Example 1

2.0 ml of a reaction solution containing the following reagents (concentration in the reaction mixture: 100 mM Tris/HCl, pH 7.5; 11.3 mM oxoglutarate; 160 µM NADH; 91 µM pyridoxal 5-phosphate; 6.2 KU/l GOT; 49.6 KU/l MDH) are added to 0.2 ml of sample solution (100; 200; 300; 400; 500 mg of aspartame/l; water in the blank), 5 minutes are allowed to elapse, and extinction $E_1$ is then measured. After that, 0.2 ml of pronase E solution (5. mg of pronase E in 1 ml of 125 mM Tris/HCl, pH 7.5) is added. After 20 minutes, extinction $E_2$ is measured. The results are evaluated by plotting the extinction differences ($\Delta E$) against the standard concentrations:

$$\Delta E_{Bl} = E_1 - E_2$$

$$\Delta E_{Sa} = E_1 - E_2$$

$$\Delta E = \Delta E_{Sa} - \Delta E_{Bl}$$

Bl=blank
Sa=sample/standard

Under the reaction conditions described, there is a linear relationship between the measured signal ($\Delta E$) and the aspartame concentration in the sample in the range of 0–500 mg/l aspartame. A calibration curve for this range is presented in FIG. 1.

Example 2 a) Reagents for 50 test mixtures

Reagent 1: 30 ml Tris/HCl buffer solution, pH 7.5 (500 mM)

Reagent 2: 5 oxoglutarate/pyridoxal 5-phosphate tablets (63.4 mg/0.6 mg/tablet)

Reagent 3: 10 NADH tablets (1.42 mg/tablet)

Reagent 4: 1 ml of GOT/MDH suspension (750 U of GOT/6000 U of MDH/ml)

Reagent 5: 5 pronase E tablets (10 mg/tablet)

Reagent 6: 5 mg of aspartame lyophilizate

All the reagents are stable at 4° C. for at least one year.

b) Standard solutions

In order to prepare standard solutions for a calibration curve, reagent 6 is dissolved in 10 ml of doubly distilled water and diluted as follows:

| Final conc. of aspartame (mg/l) | Reagent 6 (ml) | Water (ml) |
| --- | --- | --- |
| 50 | 0.25 | 2.25 |
| 100 | 0.50 | 2.00 |
| 200 | 1.00 | 1.50 |
| 300 | 1.50 | 1.00 |
| 400 | 2.00 | 0.50 |
| 500 | 2.50 | 0.00 |

The diluted standard solutions should be stored in aliquots at −20° C.

c) Reaction solutions

In order to prepare reaction solution A, one tablet of reagent 2 and two tablets of reagent 3 are dissolved in 5 ml of reagent I and 15.5 ml of doubly distilled water in a beaker. 0.2 ml of reagent 4 is then added and the mixture is stirred carefully.

In order to prepare reaction solution B, one tablet of reagent 5 is dissolved in 0.5 ml of reagent 1 and 1.6 ml of double distilled water.

The two reaction solutions are in each case sufficient for 10 reaction mixtures. They should always be prepared freshly and used up directly after having been prepared.

d) Pipetting schedule

The additions of the two reaction solutions to the cuvettes containing sample or standard solutions should be timed.

| | Reagent blank | Standard/sample |
| --- | --- | --- |
| Water | 0.2 ml | — |
| Standard/sample | — | 0.2 ml |
| Solution A | 2 ml | 2 ml |
| Allow 5 minutes to elapse, measure $E_1$ | | |
| Solution B | 0.2 ml | 0.2 ml |
| Allow 20 minutes to elapse, measure $E_2$ | | |

Wavelength: 340 nm or 365 nm (room temperature)

Light path (cuvette): 1 cm e) Evaluation

The results can be evaluated using the slope of the calibration curve or by comparing the extinction of an unknown sample ($E_{Sa}$) with the extinction of a standard ($E_S$) of known concentration, while taking into account the blank value ($E_{Bl}$), in accordance with the following equations:

$$\Delta E_{S/Sa} = (E_{1S/Sa} - E_{2S/Sa}) - (E_{1Bl} - E_{2Bl})$$

$$C_P = \frac{\Delta E_{Sa}}{\Delta E_S} \cdot C_S$$

Example 3

Determination of aspartame in foodstuffs

Comparison of the HPLC method with the method according to the invention

In order to determine the aspartame content of various foodstuffs, the samples were prepared both for the HPLC determination and the enzyme test as follows:

The drink samples were degassed by being briefly shaken and were then filtered;

Sweets, granulated sweeteners and sweetener tablets were weighed, dissolved in defined quantity in 10 ml of doubly distilled water, and thin filtered.

The aspartame content in the sample solutions prepared in this way was determined by the HPLC method (Amtl. Sammlung von Untersuchungsverfahren (Official Collection of Investigative Methods) in accordance with §35 LMBG (Law relating to Foodstuffs), L 32, 13-1 of Dec. 1989) and by the method according to the invention. The results from the two determination methods are compared in the table below. Comparison of the values measured using the two methods demonstrates that the novel enzymic method described is very well suited to determining the aspartame content in foodstuffs. Measurement of the 10 samples by the HPLC method took about five times as long as did the enzymic determination.

| | Aspartame [mg/l] | |
| --- | --- | --- |
| Sample | HPLC method | Enzymic method |
| Drink 1 | 31 | 34 |
| Drink 2 | 426 | 429 |
| Drink 3 | 471 | 487 |
| Drink 4 | 19 | 23 |
| Drink 5 | 18 | 21 |
| Sweetener tablet 1 | 163 | 161 |
| Sweetener tablet 2 | 178 | 179 |
| Granulated sweetener | 267 | 268 |
| Sweet | 96 | 95 |
| Yogurt | 43 | 39 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the enzymic determination of aspartame in an aqueous sample solution, consisting essentially of incubating the sample solution in the presence of a protease which hydrolyzes aspartame to aspartic acid and phenylalanine methyl ester, and the aspartic acid detection reagents oxoglutarate, glutamate-oxaloacetate transaminase (GOT), malate dehydrogenase (MDH) and nicotinamide adenine dinucleotide (reduced) (NADH), and, optionally, pyridoxal 5-phosphate, measuring the decrease in the NADH extinction photometrically, and determining the amount of aspartame in the sample solution by comparison with the decrease in NADH extinction in a standard solution of a known amount of aspartame; whereby the determination can be carried out in the presence of all the reagents in a single reaction vessel.

2. A method of claim 1, wherein the aspartic acid detection reagents include pyridoxal 5-phosphate.

3. A method of claim 1, wherein the incubation with the protease is carried out after the aspartic acid detection reagents are added to the sample and after the $E_1$ NADH extinction is measured photometrically.

4. A method of claim 1, wherein pronase E is used as the protease.

5. A method for the enzymic determination of aspartame in an aqueous sample solution, consisting essentially of incubating sample solution with the aspartic acid detection reagents oxoglutarate, glutamate-oxaloacetate transaminase (GOT), malate dehydrogenase (MDH) and nicotinamide adenine dinucleotide (reduced) (NADH), and, optionally, pyridoxal 5-phosphate, measuring the $E_1$ NADH extinction photometrically, adding a protease which hydrolyzes aspartame to aspartic acid and phenylalanine methyl ester to the sample solution containing said aspartic acid detection reagents, and further incubating the sample solution, measuring the decrease in the NADH extinction photometrically, and determining the amount of aspartame in the sample solution by comparison with the decrease in NADH extinction in a standard solution of a known amount of aspartame; whereby the determination can be carried out in the presence of all the reagents in a single reaction vessel.

6. A method of claim 5, wherein the aspartic acid detection reagents include pyridoxal 5-phosphate.

7. A composition for the enzymic determination of aspartame in aqueous solutions, consisting essentially of effective amounts of oxoglutarate, GOT, MDH, NADH and a protease, and, optionally, pyridoxal 5-phosphate.

8. A composition of claim 7, wherein oxoglutarate, NADH and the protease are present in solid form.

9. A composition of claim 8, wherein pyridoxal 5-phosphate in solid form is present.

* * * * *